(12) United States Patent
Kroll et al.

(10) Patent No.: US 6,813,514 B1
(45) Date of Patent: Nov. 2, 2004

(54) SYSTEM AND METHOD FOR EMULATING A SURFACE EKG USING AN IMPLANTABLE CARDIAC STIMULATION DEVICE

(75) Inventors: Mark W. Kroll, Simi Valley, CA (US); Bruce Kleine, Reseda, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 10/334,758

(22) Filed: Dec. 30, 2002

(51) Int. Cl.[7] .................................................. A61B 5/04
(52) U.S. Cl. ...................................................... 600/509
(58) Field of Search ................................ 600/508, 509, 600/512, 513, 523

(56) References Cited

U.S. PATENT DOCUMENTS

| | | | |
|---|---|---|---|
| 5,058,598 A | 10/1991 | Nicklaus et al. | 128/699 |
| 5,711,304 A | 1/1998 | Dower | 128/696 |
| 5,740,811 A | 4/1998 | Hedberg et al. | 128/697 |
| 5,850,370 A | 12/1998 | Stringer et al. | 367/128 |
| 6,052,615 A | 4/2000 | Feild et al. | 600/509 |
| 6,119,035 A | 9/2000 | Wang | 600/509 |
| 6,438,409 B1 | 8/2002 | Malik et al. | 600/512 |
| 6,522,915 B1 * | 2/2003 | Ceballos et al. | 600/509 |
| 6,633,776 B2 * | 10/2003 | Levine et al. | 600/523 |

FOREIGN PATENT DOCUMENTS

| | | | |
|---|---|---|---|
| EP | 0784996 A1 | 7/1997 | A61N/1/365 |
| WO | WO 02/41772 A1 | 5/2002 | A61B/5/04 |
| WO | WO 02/034333 A3 | 5/2002 | A61N/1/375 |

OTHER PUBLICATIONS

S. Serge Barold et al., "The Paced 12–Lead Electrocardiogram Should No Longer Be Neglected in Pacemaker Follow–up," PACE 2001; 24:1455–1458.

* cited by examiner

Primary Examiner—George Manuel

(57) ABSTRACT

A surface electrocardiogram (EKG) is emulated using signals detected by the internal leads of an implanted device. The emulation is performed using a matrix-based technique that separately emulates each of the individual signals of a multiple-lead EKG, rather than merely emulating a single combined EG. In one example, each of the twelve signals of a standard 12-lead EKG are individually emulated, allowing for separate processing and display. The emulation technique takes into account factors affecting the relative locations of the internal leads, such as respiration and posture, to thereby provide a more accurate emulation. A calibration technique is provided for calibrating the EKG emulation for use with a particular patient and a verification technique is provided for automatically verifying the reliability of the emulation. Any significant loss in emulation reliability is likely caused by lead dislodgment and so automatic detection of possible lead dislodgment is also achieved.

16 Claims, 10 Drawing Sheets

SYSTEM AND METHOD FOR EMULATING A SURFACE EKG USING AN IMPLANTABLE CARDIAC STIMULATION DEVICE

CROSS-REFERENCE TO RELATED APPLICATIONS

This application is related to U.S. patent application Ser. No. 10/334,741, entitled "System and Method for Emulating a Surface EKG Using an Implantable Cardiac Stimulation Device," and U.S. patent application Ser. No. 10/334,738, entitled "System and Method for Emulating a Surface EKG Using an Implantable Cardiac Stimulation Device," both filed concurrently herewith.

FIELD OF THE INVENTION

The invention generally relates to implantable medical devices, such as pacemakers or implantable cardioverter-defibrillators ("ICDs") and to external programmers for use therewith and, in particular, to techniques for emulating a surface electrocardiogram (EKG) based on internal electrical cardiac signals.

BACKGROUND OF THE INVENTION

A pacemaker is a medical device, typically implanted within a patient, which recognizes various arrhythmias such as an abnormally slow heart rate (bradycardia) or an abnormally fast heart rate (tachycardia) and delivers electrical pacing pulses to the heart in an effort to remedy the arrhythmias. An ICD is a device, also implantable into a patient, which additionally recognizes atrial fibrillation (AF) or ventricular fibrillation (VF) and delivers electrical shocks to terminate fibrillation. Pacemakers and ICDs detect arrhythmias by sensing internal electrical cardiac signals using leads mounted within the heart. The internal signals comprise an intracardiac electrogram (IEGM). More specifically, the normal contraction of atrial heart muscle tissue appears as a P-wave within the IEGM. A sequence of consecutive P-waves defines the atrial rate. The normal contraction of ventricular muscle tissue appears as an R-wave (sometimes referred to as the "QRS complex") within the IEGM.

Pacemakers and ICDs are often configured to be used in conjunction with a programmer that allows a physician to program the operation of the implanted device to, for example, control the specific parameters by which the device detects arrhythmia conditions and responds thereto. For example, the programmer may allow the physician to specify the sensitivity with which the implanted device senses electrical signals within the heart and to further specify the amount of electrical energy to be employed for pacing the heart in circumstances where expected heart signals are not sensed. Additionally, the programmer may be configured to receive and display a wide variety of diagnostic information detected by the implanted device, such as graphs of the IEGM sensed by the implanted device. In addition, the programmer may operate to analyze the data received from the device to assist the physician in rendering diagnoses as to possible arrhythmias and to assist the physician in programming the device to provide appropriate therapy.

Current state of the art implantable cardiac stimulation devices may have dozens or hundreds of programmable parameters that can be individually programmed using the external programmer. The programmable parameters permit the operation of the cardiac stimulation device to be tailored to the needs of the particular patient to provide optimal therapy while minimizing the risk of any unnecessary therapy. Unfortunately, it is often difficult to predict what the resultant operation will be for any given patient with any selected set of parameter settings. Hence, a potentially viable set of parameters is chosen by the physician, the implantable cardiac stimulation device is programmed using the selected set of parameters, and then the patient is sent home. Weeks or months later the patient must return to the physician's office for a follow-up appointment so that they physician may evaluate the results of the selected parameters.

Typically, the follow-up evaluation consists of the physician making judgments based upon a review of diagnostic information provided by the implanted device (including the IEGM) in combination with a 12-lead surface electrocardiogram (EKG or ECG) provided by a separate surface EKG unit. The 12-lead EKG unit provides twelve separate signals (detected using electrodes attached to different locations on the patient) that can be individually processed, displayed and reviewed or can be combined to yield a single combined surface EKG. As part of the review, the physician often needs to compare new 12-lead surface EKGs with recorded 12-lead surface EKGs from previous sessions. In any case, the physician adjusts the programming of the implanted device to improve therapy delivered to the patient. Again, the patient is sent home for several more weeks or months until another follow-up visit. This cycle may be repeated numerous times before optimal device settings are determined by the physician.

To obtain a 12-lead surface EKG, ten electrodes are manually attached the skin of the patient in the configuration shown in FIG. 1. The surface EKG derived from the ten electrodes is referred to as a "12-lead" EKG because twelve signals are derived from the ten electrodes—including signals from individual electrodes plus signals between certain pairs of the physical leads. More specifically, the ten electrodes include four limb electrodes and six "chest" electrodes. The chest electrodes are labeled: $V_1$–$V_6$. The limb electrodes are: RA (right arm), LA (left arm), LL (left leg) and right leg (RL), the last of which is optional The chest electrodes provide one signal per electrode, referred to as the $V_1$–$V_6$ signals. The RA, LA and LL limb electrodes also provide one signal per electrode, referred to as the aVR, aVL and aVF signals (with F signifying foot as opposed to leg.) Finally, the difference between each pairing of the RA, LA and LL limb electrodes is considered a separate "lead" (referred to as the Einthoven leads I, II and III) and hence provide the last three signals of the 12-lead surface EKG. The twelve signals of the 12-lead surface EKG are summarized in TABLE I, along with the electrodes from which the signals a rederived.

TABLE I

| PHYSICAL LEADS | SURFACE EKG SIGNALS |
| --- | --- |
| $V_1$ | $V_1$ |
| $V_2$ | $V_2$ |
| $V_3$ | $V_3$ |
| $V_4$ | $V_4$ |
| $V_5$ | $V_5$ |
| $V_6$ | $V_6$ |
| LA - RA | I |
| LL - RA | II |
| LL - LA | III |
| RA | aVR |

TABLE I-continued

| PHYSICAL LEADS | SURFACE EKG SIGNALS |
|---|---|
| LA | aVL |
| LL | aVF |

It is particularly important to review the 12-lead surface EKG during follow-up sessions. See: "The Paced 12-Lead Electrocardiogram Should No Longer Be Neglected in Pacemaker Follow-Up", by S. Serge Barold; Paul A. Levine; I. Eli Ovsyshcher, PACE 2001; 24:1455–1458. However, the need to manually attach and remove each of the surface EKG electrodes from the patient during each follow-up session is a burden to the physician (or his or her staff) and a considerable inconvenience to the patient. In many cases, the skin of the patient must be shaved and sanded in the locations where the electrodes are to be attached to provide adequate electrical conduction. This can be quite uncomfortable and, in some cases, embarrassing for the patient. Moreover, the time required to attach and then remove the electrodes adds to the overall cost of the follow-up session. Also, from one follow-up session and another, the electrodes may not be placed at the exact same locations on the patient, thus resulting in somewhat different surface EKGs and making it more difficult for the physician to properly identify any actual differences in cardiac signals of the patient from one session to the next.

As can be appreciated, it would be desirable to eliminate the need for attaching the electrodes of the 12-lead surface EKG to patients during follow-up sessions to thereby reduce the cost and inconvenience to the patient and to eliminate problems resulting form differing electrode placement. One proposed solution is to emulate the surface EKG using internal electrical cardiac signals sensed by the implanted device so that, during a follow-up session, a separate surface EKG system is not required and external electrodes need not be attached to the patient. One technique for emulating a surface EKG using internal electrical signals is described in U.S. Pat. No. 5,740,811 to Hedberg et al., entitled "Device and Method for Generating a Synthesized ECG", which is incorporated by reference herein. With the technique of Hedberg et al., a neural network is employed to convert electrical signals derived from implanted electrodes into a single emulated or "synthesized" surface EKG.

The technique of Hedberg et al. achieves significant improvement by eliminating the need to use a separate surface EKG unit during follow-up sessions. However, there is considerable room for further improvement. The neural network technique of Hedberg et al. appears to emulate only a single combined EKG and does not emulate each of the twelve individual signals of the conventional 12-lead EKG. Hence, the physician cannot review the individual signals nor use any hardware or software adapted for separately processing the individual signals. Accordingly, it would be desirable to provide a surface EKG emulation technique that separately emulates each of the twelve signals of a conventional 12-lead EKG and it is to this end that aspects of the invention are directed.

In addition, the technique of Hedberg et al. does not appear to take into account factors affecting the relative locations of implanted electrodes during the emulation. In particular, respiration, posture and the beating of the various chambers of the heart all affect the relative locations of internal electrodes—both with respect to one another and with respect to the locations of surface electrodes of the EKG being emulated—and hence affect the accuracy of EKG emulation. Respiration causes the heart to twist slightly thus changing the relative locations of electrodes mounted within the heart, particularly with respect to the location of the device can. The beating of the various chambers of the heart during different phases of a cardiac cycle also change the relative locations of the electrodes. Differences in overall patient posture (i.e. whether the patient is sitting, standing, or lying down) also affect the location of the device can and the location of the heart and another internal organs and hence affect the relative locations of the internal electrodes. Without taking these factors into account, precise EKG emulation is not achieved. Accordingly, it would be desirable to provide a surface EKG emulation technique that takes into account factors affecting the relative locations of internal electrodes and it is to this end that aspects of the invention are directed.

Still other aspects of the invention are directed to providing a calibration technique for calibrating the surface EKG emulation for use with a particular patient and a verification technique for automatically verifying the reliability of the surface EKG emulation. Any significant change in the reliability of the surface EKG emulation is likely caused by lead dislodgment. Hence, the invention also provides a technique for automatically detecting possible lead dislodgment.

SUMMARY

In accordance with one illustrative embodiment, a method is provided for emulating individual signals of a multiple-lead surface EKG of a patient in which an implantable cardiac stimulation device is implanted. The method includes inputting electrical cardiac signals sensed using a combination of pairs of electrodes implanted within the patient; and then emulating each of a plurality of separate signals associated with the multiple-lead surface EKG based on the input electrical cardiac signals.

For example, each of the twelve signals associated with a standard 12-lead surface EKG can be emulated, i.e. the technique provides for separate emulated $V_1$, $V_2$, $V_3$, $V_4$, $V_5$, $V_6$, I, II, III, aVR, aVL, and aVF signals.

The emulation technique may be performed by the implanted device itself or by an external device, such as an external programmer, configured to receive the electrical cardiac signals from the implanted device. In either case, by emulating each of the individual signals of the surface EKG, rather than merely generating a combined surface EKG signal, the separate signals can be individually processed using any of a wide variety of techniques, conventional or otherwise. For example, the individual signals can be filtered separately and displayed separately. All or just a selected portion of the individual signals can be combined, perhaps with the individual signals weighted differently, to generate a single surface EKG for actual display. Hence, a great deal more flexibility is achieved than with emulation systems that merely generate a single combined surface EKG.

Preferably, when the technique is performed by the implanted device, it does so only while in communication with the external programmer. In other words, the implanted device only emulates the surface EKG signals while in telemetry contact with the external programmer. Hence, the implanted device need only transmit the emulated surface EKG signals to the external programmer and so the emulated EKG signals need not be stored within the memory of the implanted device. However, in other implementations, the implanted device operates to continuously emulate the surface EKG at all times. If so, the emulated surface EKG is stored within the memory of the implanted device for subsequent transmission to the external programmer, perhaps during a follow-up session with the physician. In this manner, a diagnostic record of the emulated surface EKG of the patient is recorded within the implanted device (limited only by the memory constraints of the implanted device) for subsequent review by the physician. In addition, the emulated surface EKG can be used in conjunction with an IEGM to aid in the control of delivery of therapy, such as to aid in identifying the onset of AF or VF. Hence, the technique of the invention is not limited to being performed by the implanted device only while in telemetry contact with the external programmer.

In an exemplary embodiment, emulation of the individual signals is 20 performed using a matrix-based technique. A combination of pairs of internal electrodes is selected and cardiac signals sensed using the selected pairs of electrodes are input. The input signals are converted into a time-varying vector F(t) having individual elements corresponding to the pairs of electrodes. Then, a conversion matrix M is input, which is composed of weighting factors representative of the relative extent to which the signals derived from the selected pairs of electrodes influence surface voltages at locations corresponding to the multiple-lead surface EKG being emulated. Finally, a time-varying vector E(t) is generated by calculating: E(t)=$\underline{M}$*F(t). The individual time-varying elements of E(t) represent the individual emulated surface EKG signals. In an example wherein ten pairs of electrodes are selected to emulated a 12-lead surface EKG, vector F(t) has ten elements and conversion matrix $\underline{M}$ is a ten by twelve matrix thus providing an output vector E(t) with twelve elements corresponding to the twelve leads of the 12-lead surface EKG. In general, though, the selected combination of electrodes includes N pairs of electrodes and the surface EKG to be emulated includes M surface leads. F(t) has N elements, n=1, 2, . . . , N; E(t) has M elements, m=1, 2, . . . , $\underline{M}$; and $\underline{M}$ is an N by M matrix containing weighting factors $K_n^m$ representative of the extent to which the internal voltage derived from electrode pair n influences the surface voltage at surface lead m.

With the matrix-based technique, virtually any combination of pairs of internal electrodes can be used to emulate the surface EKG. Hence, the technique can be applied to a wide variety of implantable cardiac stimulation systems having a wide variety of lead arrangements. In additon, the technique can be used to emulate surface EKG signals for any number and combination of surface leads and locations, such as 10-lead EKGs, 6-lead EKGs, etc. Thus, again, great flexibility is provided. For a given internal lead arrangement, the combination of electrodes that achieves the most accurate surface EKG emulation is typically selected for use. In other cases, however, to gain a reduction in processing and memory resources, some other combination of electrode pairs is employed, which may not provide the highest degree of accuracy in the emulation.

In addition, in the exemplary embodiment, cross-correlation values of certain elements of vector F(t), which should not change significantly with time, are calculated and compared against baseline cross-correlation values to verify the reliability of the emulation. If the cross-correlation values differ significantly from the baseline values, the emulation is deemed to be unreliable. This may be caused by lead dislodgment. Hence, the invention also provides for automatic detection of possible lead dislodgment.

In accordance with a second aspect of the invention, a method is provided for emulating a multiple-lead surface EKG of a patient in which an implantable cardiac stimulation device is implanted wherein the emulation takes into account factors affecting the relative locations of leads implanted within the patient such as respiration, posture and phase of cardiac cycle. The method includes the steps of: inputting electrical cardiac signals sensed using a combination of pairs of implanted electrodes; inputting a signal representative of factors affecting the positions of the electrodes; and generating an emulated surface EKG based on the electrical cardiac signals while taking into account the factors affecting the positions of the electrodes. By taking into account such factors as respiration, phase of cardiac cycle, and posture, a more accurate emulation of the surface EKG is achieved that compensates for movement of the internal electrodes relative to one another and relative to the lead locations of the surface EKG being emulated.

In the exemplary matrix-based implementation, slightly different separate conversion matrices are used depending upon the factors affecting the relative locations of the internal electrodes. Alternatively, the weighting factors $K_n^m$ of a single conversion matrix $\underline{M}$ are adjusted. If multiple factors affecting relative lead location are to be compensated for simultaneously, then either the separate conversion matrices are averaged together to yield a single adjusted matrix $\underline{M}$ or the weighting values of the single matrix $\underline{M}$ are adjusted. In any case, by compensating for movement of the internal electrodes, a far more accurate and reliable emulation of the surface EKG is achieved. Indeed, the emulated surface EKG may be more reliable than an actual surface EKG. As noted above, variation in placement of the surface electrodes on the skin of the patient from one session to another can result in unintended variations in the surface EKG. By instead generating a surface EKG using internal signals and by compensating for the relative movement of the internal leads, a more accurate, reliable and consistent surface EKG is thereby generated.

In accordance with a third aspect of the invention, a calibration or set-up method is provided for calibrating a surface EKG emulation technique. The calibration method is performed by external programmer in combination with an implantable cardiac stimulation device implanted within a patient and a multiple-lead surface EKG unit. Separate initial multiple-lead surface EKG signals are input to the external programmer from the EKG unit as detected using separate surface electrodes attached to the patient. Initial internal electrical cardiac signals sensed by the implanted device using internal electrodes are also input to the external programmer. A set of conversion values for converting internal cardiac signals into separate multiple-lead surface EKG signals are then generated, based on a comparison of the initial surface EKG signals and the initial internal cardiac signals. Then, separate multiple-lead surface EKG signals are emulated based on newly sensed internal electrical cardiac signals using the conversion values. Once the conversion values have been generated, actual emulation of the surface EKG signals may be performed either by the external programmer or by the implanted device. In any case, with this set-up technique, the emulation process is thereby calibrated for use with a particular patient based on surface EKG signals detected for that patient.

When using the exemplary matrix-based implementation, the set of conversion values is generated as follows. The initial internal cardiac electrical signals are converted into a time-varying vector F(t) having individual elements corresponding to the various pairs of electrodes. The initial surface EKG signals are converted into a time-varying vector E(t) having individual elements corresponding to the surface leads A time-varying conversion matrix $\underline{M}(t)$ of weighting factors is generated by calculating $\underline{M}(t)=E(t)*F^{-1}(t)$. The time-varying conversion matrix $\underline{M}(t)$ is averaged over time to yield a fixed matrix $\underline{M}$ for use in converting newly-sensed internal cardiac signals into surface EKG signals. Thus, this provides a technique for generating an individual conversion matrix $\underline{M}$. As noted, multiple conversion matrices may be used depending upon the implementation. For example, if factors affecting the relative locations of the internal electrodes are to be subsequently detected and compensated for during EKG emulation, then during the setup process either separate individual conversion matrices are generated and stored using this technique or a single conversion matrix is generated and then values for adjusting the weighting values $K_n^m$ of the single conversion matrix are generated and stored.

Thus, in its various embodiments, the invention provides for emulation of the separate signals of surface EKGs while taking into account factors affecting the relative locations of internal electrodes. The invention also provides a calibration technique for calibrating the surface EKG emulation for use with a particular patient and a verification technique for automatically verifying the reliability of the surface EKG emulation. The invention also provides a technique for automatically detecting possible lead dislodgment. Other objects, features and advantages of the invention will be apparent from the descriptions below in combination with the accompanying drawings.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Implantable Device Overview

Figure 1:
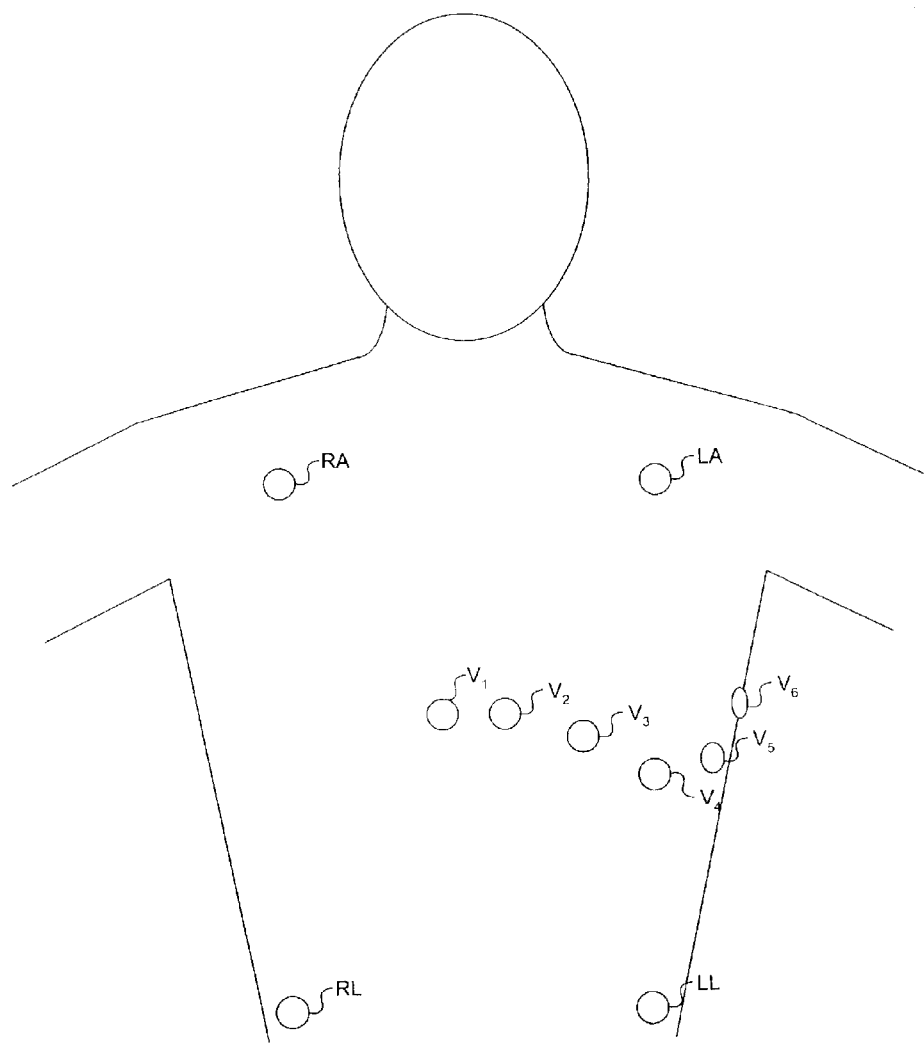
FIG. 1 is a diagram illustrating a system of electrodes for use in generating a 12-lead surface EKG in accordance with the prior art.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

Figure 2:
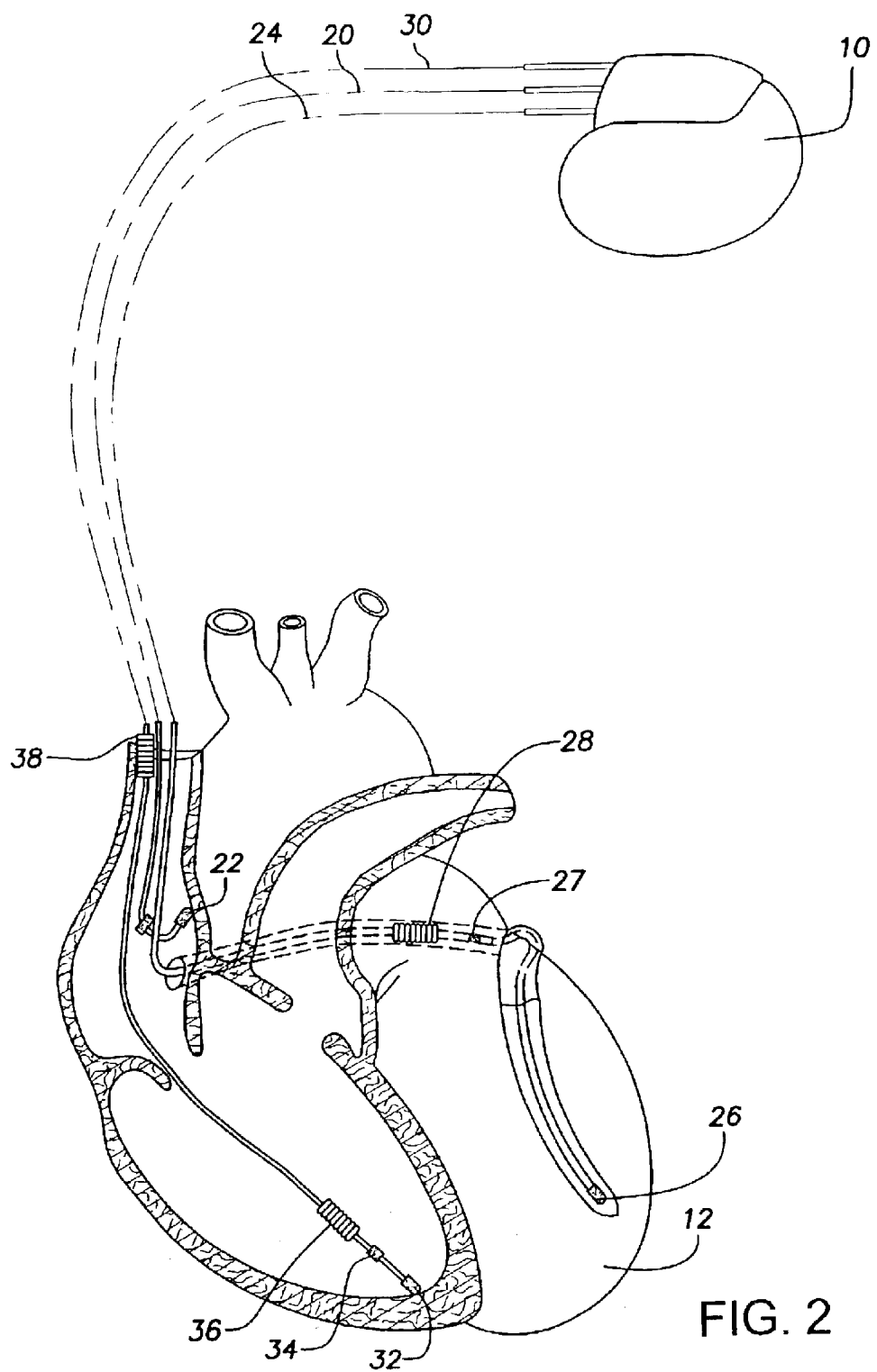
FIG. 2 is a simplified diagram illustrating an implantable stimulation device in electrical communication with at least three leads implanted into a patient's heart for delivering multi-chamber stimulation and shock therapy.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle. Although not show, the system of leads may also include one or more RA rings in the proximal coronary sinus, one or more LV rings and an LV coil As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36. and 38, for shocking purposes. The housing 40 further includes a connector (not shown) having a plurality of terminals, 42, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. Additional terminals may be provided for use with RA rings, LV rings or an LV coil.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to sense voltages between any of the electrodes of the right atrial lead 20, coronary sinus lead 24, and the right ventricular lead 30, and the can, through the switch 74 for sensing the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), as is known in the art.

Microcontroller 60 includes an on-board surface EKG emulation system 101, which operates to convert internal cardiac electrical signals received from the electrodes into 12-lead surface EKG signals so as to emulate a surface EKG, in accordance with a technique to be described in detail below with reference to FIGS. 5–12. As part of the emulation process, the emulation system takes into account the current phase of the cardiac cycle of the patient, the current phase of the respiratory cycle of the patient, and the current posture of the patient. The current phase of the cardiac cycle is derived from the internal electrical cardiac signals. The current phase of the respiratory cycle is derived from thoracic impedance values determined from a minute ventilation (MV) sensor 103 or other respiratory sensor. The posture of the patient is determined by a posture detection system 105, based upon signals received from a 3-D accelerometer 107 or other posture detection device. Although shown as external to the device, components of the accelerometer and the MV sensor alternatively may be internal to the device can.

For arrhythmia detection, the device 10 utilizes cardiac event detection unit 101 to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both chambers but only paces in the ventricle. A sensed event on the atrial channel triggers a ventricular output after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules) or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Device Programmer Overview

Figure 3:
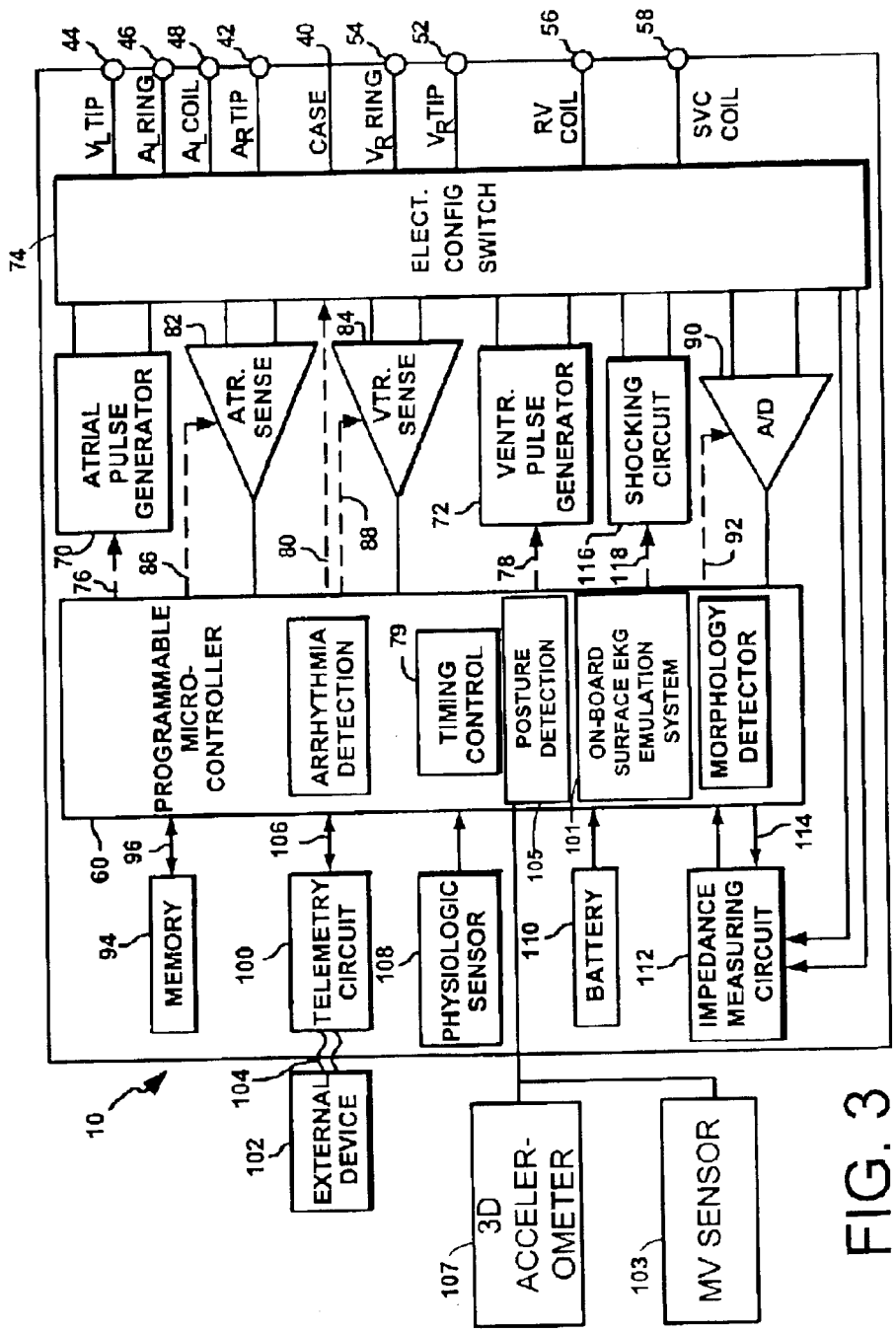
FIG. 3 is a functional block diagram of the multi-chamber implantable stimulation device of FIG. 2 illustrating the basic elements of a stimulation device which can provide cardioversion, defibrillation and pacing stimulation in four chambers of the heart and particularly illustrating an on-board surface EKG emulation system for emulating a 12-lead surface EKG using internal electrical cardiac signals derived from the leads of FIG. 2.

FIG. 3 illustrates pertinent components of an external programmer for use in programming an implantable medical device such as a pacemaker or ICD. Briefly, the programmer permits a physician or other user to program the operation of the implanted device and to retrieve and display information received from the implanted device such as IEGM data and device diagnostic data. Additionally, the external programmer receives and displays ECG data from separate external ECG leads that may be attached to the patient. Depending upon the specific programming of the external programmer, programmer 200 may also be capable of processing and analyzing data received from the implanted device and from the ECG leads to, for example, render preliminary diagnosis as to medical conditions of the patient or to the operations of the implanted device.

Now, considering the components of programmer 200, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206 and random access memory 230. Additional software may be accessed from a hard drive 208, floppy drive 210 and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an emergency VVI (EVVI) key. The EWI key sets the implanted device to a safe VVI mode with high pacing outputs. This ensures life sustaining pacing operation in nearly all situations but by no means is it desirable to leave the implantable device in the EVVI mode at all times.

Typically, the physician initially controls the programmer 200 to retrieve data stored within the implanted medical device and to retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via internal bus 204. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient near the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted device is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 200, the implanted device may be further controlled to transmit additional data in real time as it is detected by the implanted device, such as additional IEGM data, lead impedance data, and the like. Additionally, or in the alternative, telemetry subsystem 222 receives ECG signals from ECG leads 232 via an ECG processing circuit 234. As with data retrieved from the implanted device itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time.

Thus, the programmer receives data both from the implanted device and from the external ECG leads. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 28 to thereby reprogram the implanted device. Prior to reprogramming specific parameters, the physician may control the external programmer to display any or all of the data retrieved from the implanted device or from the ECG leads, including displays of ECGs, IEGMs and statistical patient information. Any or all of the information displayed by programmer may also be printed using a printer 236.

Figure 10:
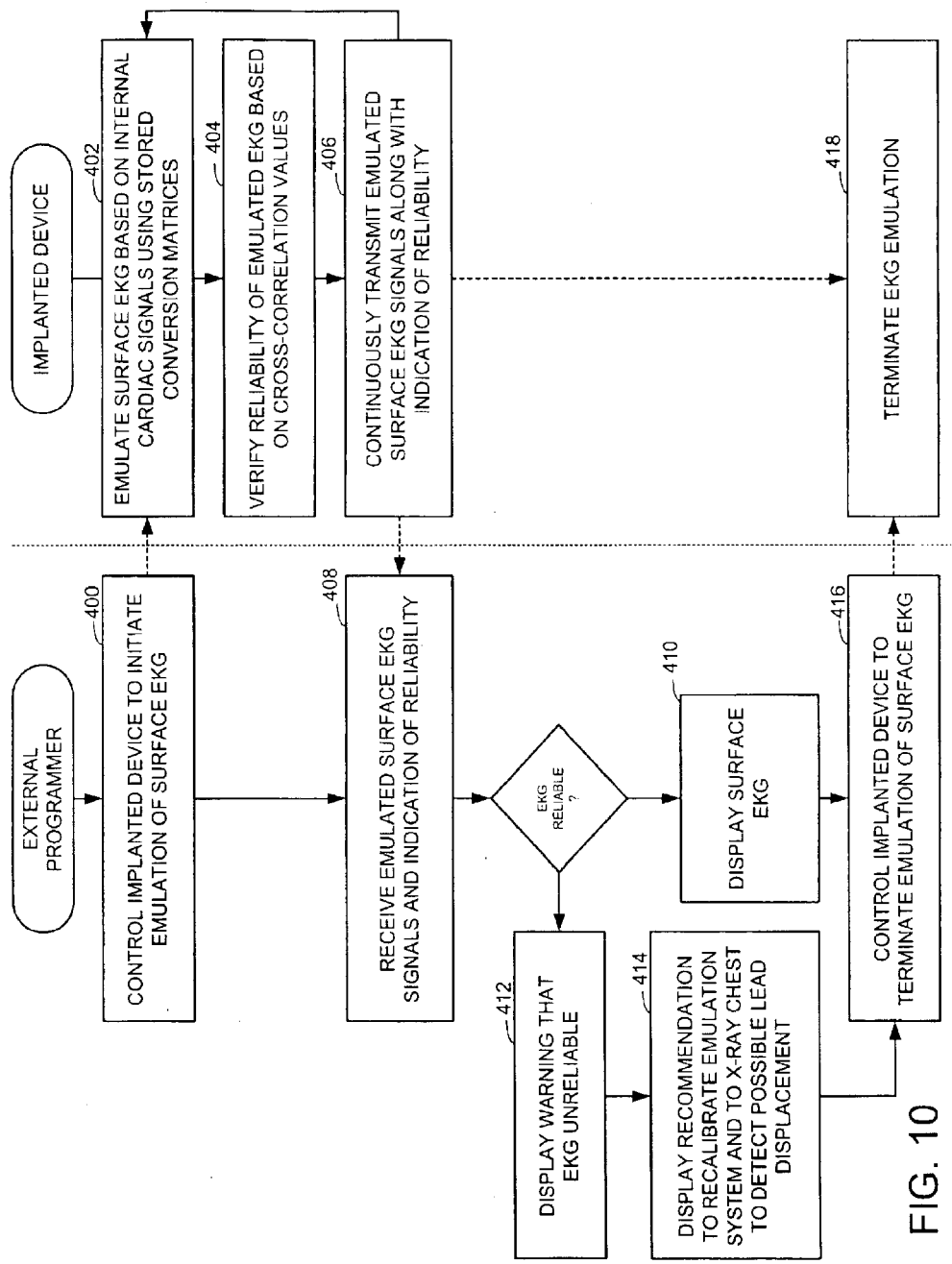
FIG. 10 is a flow chart illustrating a first exemplary implementation wherein the implanted device of FIG. 3 generates the emulated EKG for transmission to the external programmer of FIG. 4.
Figure 11:
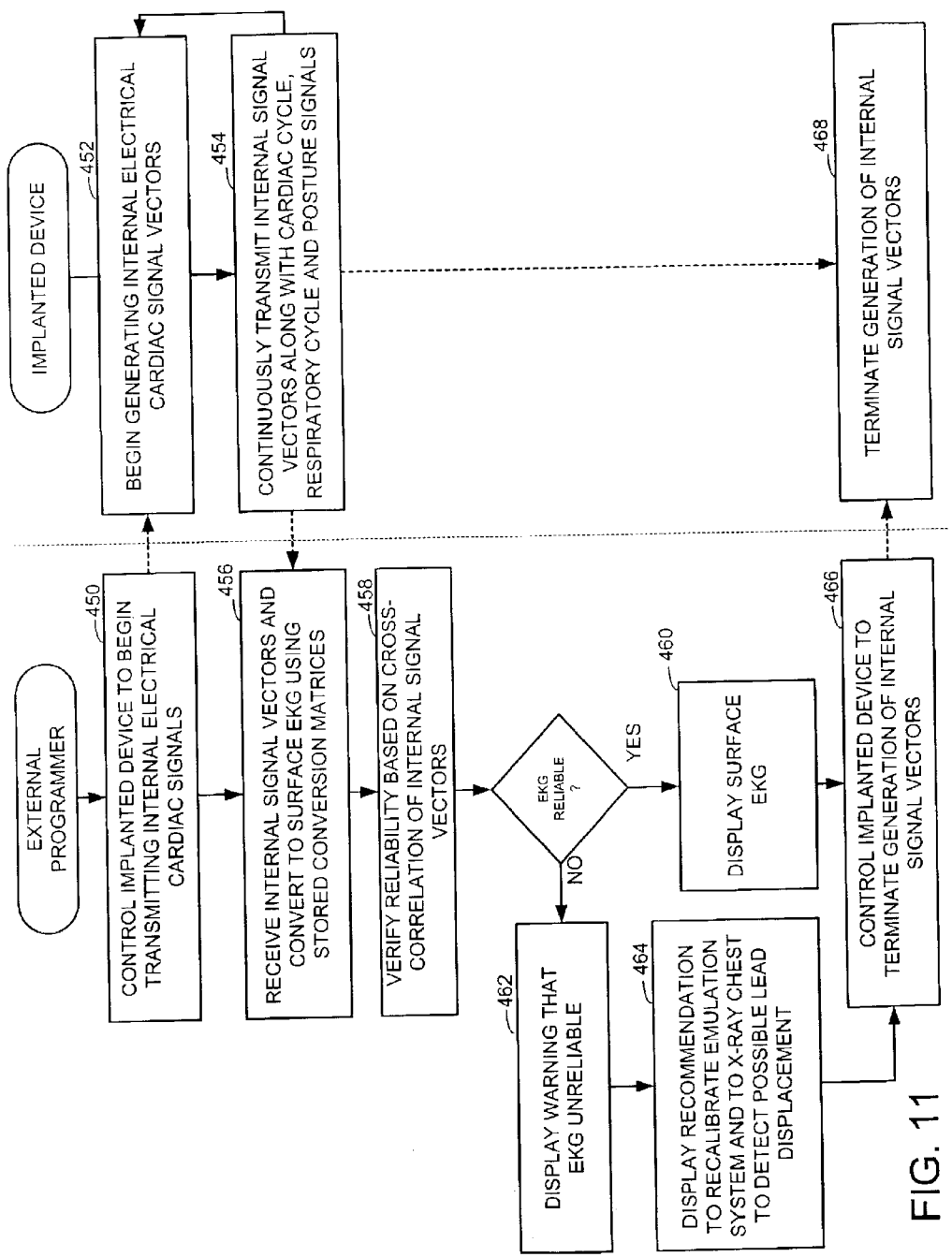
FIG. 11 is a flow chart illustrating a second exemplary implementation wherein the implanted device of FIG. 3 transmits signal vectors to the external programmer of FIG. 4, which then generates the emulated surface EKG using the signal vectors.

CPU 202 includes a programmer-based surface EKG emulation system 250 for converting internal electrical cardiac signals detected by the implanted device into a 12-lead surface IEKG. The programmer-based system is provided such that, if the implanted device does not include an on-board emulation system (i.e. system 101 of FIG. 3), the surface EKG can be emulated by the external programmer. In either case, a surface EKG emulation setup system 252 is provided to generate various conversion matrices and cross-correlation baseline values for use by either the onboard EKG emulation system or the programmer-based emulation system. A general description of the technique for emulating the 12-lead surface EKG is provided below with reference to FIGS. 5–9. FIG. 10 illustrates the operation of the external programmer and the implanted device for an embodiment wherein the implanted device performs the actual surface EKG emulation. FIG. 11 illustrates the operation of the external programmer and the implanted device for an embodiment wherein the external programmer performs the actual surface EKG emulation. The operation of the setup unit is described primarily with reference to FIG. 12.

Programmer 200 also includes a modem 238 to permit direct transmission of data to other programmers via the public switched telephone network (PSTN) or other interconnection line, such as a T1 line or fiber optic cable. Depending upon the implementation, the modem may be connected directly to internal bus 204 may be connected to the internal bus via either a parallel port 240 or a serial port 242. Other ripheral devices may be connected to the external programmer via rallel port 240 or a serial port 242 as well. Although one of each is hown, a plurality of input output (IO) ports might be provided.

A speaker 244 is included for providing audible tones to the user, uch as a warning beep in the event improper input is provided by the hysician. Telemetry subsystem 222 additionally includes an analog utput circuit 246 for controlling the transmission of analog output signals, uch as IEGM signals output to an ECG machine or chart recorder.

With the programmer configured as shown, a physician or other user operating the external programmer is capable of retrieving, processing and displaying a wide range of information received from the ECG leads or from the implanted device and to reprogram the implanted device if needed. The descriptions provided herein with respect to FIG. 3 are intended merely to provide an overview of the operation of programmer and are not intended to describe in detail each and every feature of the hardware and software of the device and is not intended to provide an exhaustive list of the functions performed by the device.

Figure 4:
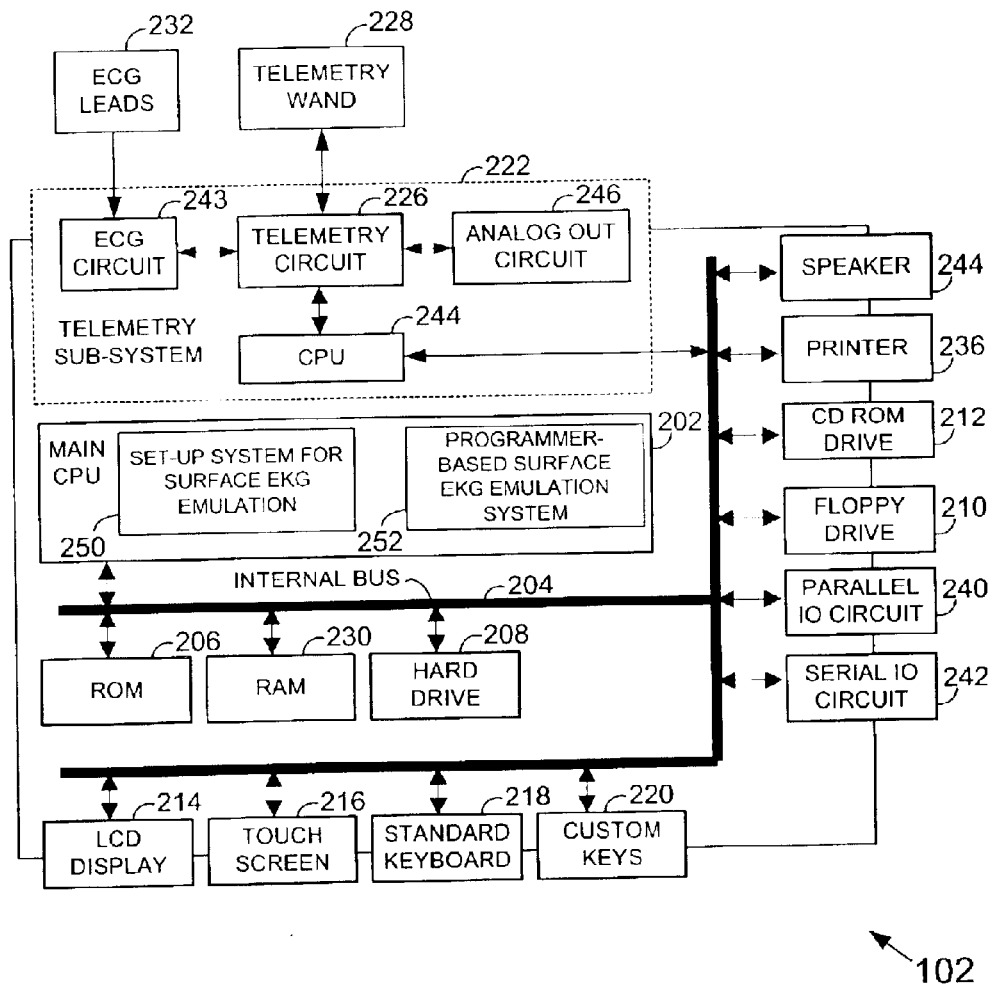
FIG. 4 is a functional block diagram illustrating components of a programmer for use in programming the implantable device of FIG. 2, and in particular illustrating a programmer-based external surface EKG emulation system for generating an emulated surface EKG based on internal electrical cardiac signals transmitted from the implanted device of FIG. 3 (particularly for use with implantable devices that do not include an on-board surface EKG emulation system) and also illustrating a surface EKG emulation set-up system for use in pre-calculating certain conversion matrices and cross-correlation values.

The operations of the implanted device of FIG. 3 and the external programmer of FIG. 4 for emulating surface EKG signals will now be described with references to the remaining figures, which include various flow-charts. In the flow charts, the various algorithmic steps are summarized in individual "blocks". Such blocks describe specific actions or decisions that must be made or carried out as the algorithm proceeds Where a microcontroller (or equivalent) is employed, the flow charts presented herein provide the basis for a "control program" that may be used by such a microcontroller (or equivalent) to effectuate the desired control of the stimulation device or external programmer. Those skilled in the art may readily write such a control program based on the flow charts and other descriptions presented herein.

EKG Emulation Overview

Referring and now to FIGS. 5–9, the general technique of the invention for converting internal electoral cardiac signals into 12-lead surface EKG signals will now be described. As noted above, the general technique can be performed either by the on-board emulation system of the implanted device (system 101 of FIG. 3) or by the programmer-based emulation system of the external programmer (system 250 of FIG. 4). In the following, it will be assumed that the emulation is performed by the on-board system of the implanted device but the description is generally applicable to the programmer-based system of the external programmer. Briefly, the technique operates to convert internal electrical cardiac signals detected by the implanted device into a set of 12-lead surface EKG signals (i.e. the twelve signals listed above in the TABLE I) while optionally taking into account the patient posture and the current phase of the cardiac and respiratory cycles of patients. Once the twelve signals of the surface EKG have been generated, the signals can be combined to yield a single surface EKG signal for printout or display by the external programmer. Thus, the technique obviates the need to employ an external surface EKG unit.

Figure 5:
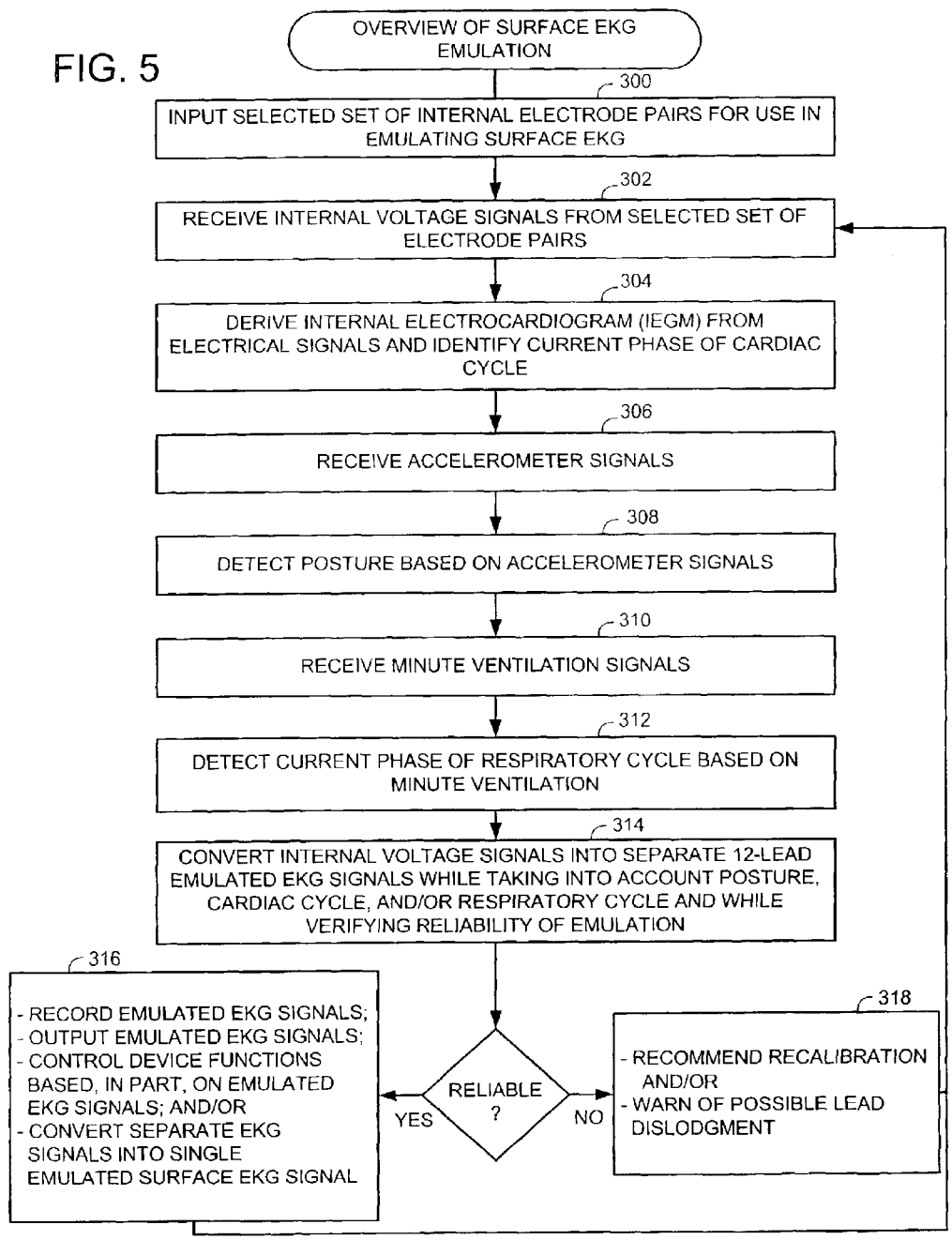
FIG. 5 is a flow chart providing an overview of an exemplary technique for converting internal electrical cardiac signals into a surface EKG for use by either the on-board surface EKG emulation system of FIG. 3 or the external surface EKG emulation system of FIG. 4.

Referring first to FIG. 5, at step 300, the on-board emulation system inputs from memory a previously selected set of internal electrode pairs for use in detecting voltage signals for emulating the surface EKG.

With the configuration of electrodes shown above in FIG. 2, literally dozens of pairs of electrodes can be chosen since, in general, voltage signals can be detected between any pair of electrodes. Hence, for example, the device can be controlled to detect the voltage between the coil of the right atrium (RA coil) and the can of the device or the device can be controlled to detect the voltage between the tip of the right atrium (RA tip) and the coil of the right ventricle (RV Coil). An exemplary set of ten pairs of internal electrodes is provided in TABLE II. The voltage signal derived from each respective pair of electrodes is referred to herein as an "F" voltage signal. With 10 pairs of electrodes, 10 volts signals are derived: $F_1, F_2, \ldots, F_{10}$. However, more or fewer combinations of electrodes can instead be employed. Typically, the set of electrode pairs to be used is selected in advance by a physician using the external programmer and the selection is transmitted to the implanted device for storage therein. Alternatively, the set of electrode pairs is selected during the design phase of the implanted device and directly programmed into the implanted device.

TABLE II

| INPUT SIGNAL | INTERNAL ELECTRODE PAIRS |
| --- | --- |
| $F_1$ | Can to RV Coil |
| $F_2$ | Can to RA/SVC Coil |
| $F_3$ | RV Coil to RA/SVC Coil |
| $F_4$ | Tip to RV Coil |
| $F_5$ | Tip to Ring CS |
| $F_6$ | CS Tip to RV Coil |
| $F_7$ | CS Tip to SVC/RA Coil |
| $F_8$ | Tip to RA Coil |
| $F_9$ | RA Tip to RV Coil |
| $F_{10}$ | Can to RV Coil |

Once the combination of electrodes has been selected, the device begins to receive internal voltage signals from each pair of selected leads, at step 302. Each internal voltage signal varies with time as a result of the propagation of electrical signals within the patient and is a digitized for subsequent processing by the on-board emulation system of the microcontroller. At step 304, the microcontroller processes the internal signals to derive the IEGM and to identify the current phase of the cardiac cycle, i.e. to determine whether the heart of the patient is currently undergoing a P-wave, an R-wave, a T-wave, or is in some segment therebetween. At step 306, the implanted device receives accelerometer signals (from accelerometer 107 of FIG. 3) and, at step 308, detects the current posture of the patient based on the accelerometer signals. Posture is detected by the posture detection system (system 105 of FIG. 3) using any appropriate technique such as the technique described in copending U.S. patent application Ser. No. 10/329233, filed Dec. 23, 2002, of Koh et al. entitled "System and Method for Determining Patient Posture Based on 3-D Trajectory Using an Implantable Medical Device," and in copending U.S. patent application Serial No. 10/328642, filed Dec. 23, 2002, of Koh et al. entitled "System and Method for Determining Patient Posture Based on 3-D Trajectory Using an Implantable Medical Device," which are incorporated by reference herein in their entirety. At step 310, the implanted device receives minute ventilation signals from the minute ventilation sensor (sensor 103 of FIG. 3) and, at step 312, detects of the current phase of the respiratory cycle of the patient based on the minute ventilation signals. For example, the implanted device determines whether the patient is currently inhaling or exhaling.

Thus, following step 312, the implanted device has detected the current phases of both the electrical cardiac cycle and the respiratory cycle of the patient and has determined the current posture of the patient. The device has also input internal electrical voltage signals from each of the selected pairs of electrodes and has converted the signals into digital values for processing. At step 314, the on-board surface EKG emulation system then converts the internal voltage signals into separate, emulated 12-lead EKG signals while taking into account posture, cardiac cycle, and respiratory cycle. The current posture of the patient is taken into account because posture affects of the relative locations of the individual internal electrodes as well as their relative distances from the surface EKG lead locations being emulated (shown in FIG. 1). For example, depending upon whether the patient is currently standing for lying down, the location of the implanted device within the patient will vary slightly. Accordingly, the distance between the can of the implanted device and the other electrodes of the implanted system will likewise vary. Moreover, the distances between the device can and each of the surface EKG locations to be emulated will vary as well. The current phase of the respiratory cycle of the patient is taken into account because respiration tends to cause the heart to twist slightly within the patient thus also affecting the relative locations of the internal electrodes. The current phase of the cardiac cycle of the patient is taken into account because the beating of the chambers of the heart also affects the relative locations of the individual internal electrodes. Hence, by taking posture, respiratory cycle and cardiac cycle into account, a more precise and reliable conversion of internal electrical signals into surface EKG signals can be achieved. The conversion process performed at step 314 is described in detail and with reference to the exemplary technique of FIGS. 6–9.

At step 314, the implanted device also verifies the reliability of the emulation. An exemplary verification technique is described in detail below. If the emulation is deemed to be reliable, then at step 316, any of the twelve individual surface EKG lead signals can be recorded or output for display/print-out or used to control device functions. In addition, at step 316, the separate EKG signals are optionally combined into a single emulated surface EKG signal, which provides a single amplitude as a function of time. Any of a wide variety of conventional techniques for converting individual 12-lead EKG signals into a single surface EKG signal may be employed. If the emulation is deemed unreliable, then at step 318, the device generates warning signals advising that the emulation process be recalibrated. A likely cause of an unreliable emulation is lead dislodgment. Hence, at step 318, signals are also generated warning of possible lead dislodgment and recommending that the patient be X-rayed.

Note that, in a preferred implementation, when the technique is performed by the implanted device it does so only while in communication with the external programmer. In other words, the on-board emulation system only emulates the surface EKG signals while in telemetry contact with the external programmer. Hence, in the preferred implementation, the implanted device need only transmit the emulated surface EKG signals to the external programmer and so the emulated EKG signals need not be stored within the memory of the implanted device. However, in other implementations, the on-board emulation system operates to continuously emulate the surface EKG at all times. If so, the emulated surface EKG is stored within the memory of the implanted device for subsequent transmission to the external programmer, perhaps during a follow-up session with the physician. In this manner, a diagnostic record of the emulated surface EKG of the patient is recorded within the implanted device (limited only by the memory constraints of the implanted device) for subsequent review by the physician.

Insofar as the control of device functions using emulated EKG signals is concerned, this may be optionally performed in implementations wherein the implanted device emulates the surface EKG at all times. Control of device functions, such as control of therapy, is preferably performed in conjunction with IEGM signals. In this regard, circumstances may arise wherein an analysis of IEGM signals alone fails to allow the microcontroller to unambiguously determine the appropriate therapy to deliver to the patient (such as to determine, for example, whether the patient is undergoing atrial fibrillation for purposes of triggering delivery of a cardioversion shock) and analysis of the emulated surface EKG can help the system select the correct course of therapy.

Although described with reference to an example wherein cardiac cycle, posture and respirator cycle are each taken in to account in the emulation of the surface EKG, in other implementations only certain combinations of these factors are considered. Indeed, none of these factors necessarily needs to be considered. However, consideration of each of these factors is preferred as it provides for the most accurate emulation of the surface EKG. In addition, other factors affecting the relative locations of the internal leads can be detected and used in the emulation process:

Exemplary Internal Signal to Surface EKG Signal Conversion Process

Thus, FIG. 5 provides an overview of the technique for emulating 12-lead surface EKG signals while taking into account posture and the current phases of the cardiac and respiratory cycle to the patient. Referring now to FIGS. 6–9, details of an exemplary matrix-based technique for converting internal voltage signals to separate emulated 12-lead EKG signals (for use at step 314 of FIG. 5) will now be described. Briefly, the technique employs a matrix $\underline{M}$ for converting a vector F representative of the internal voltage signals received from the selected pairs of electrodes into an output vector E (shown below in TABLE III) representative of the 12-lead surface EKG signals. As will be explained, the particular values for use in matrix $\underline{M}$ at any given point in time depend upon the current posture, the phase of cardiac cycle, and/or the phase of respiratory cycle of the patient. Values for use within the matrix $\underline{M}$ may be predetermined during a setup phase by the external programmer.

TABLE III

| OUTPUT SIGNAL | CORRESPONDING SURFACE LEAD SIGNAL |
|---|---|
| $E_1$ | $V_1$ |
| $E_2$ | $V_2$ |
| $E_3$ | $V_3$ |
| $E_4$ | $V_4$ |
| $E_5$ | $V_5$ |
| $E_6$ | $V_6$ |
| $E_7$ | I |
| $E_8$ | II |
| $E_9$ | III |
| $E_{10}$ | aVR |
| $E_{11}$ | aVL |
| $E_{12}$ | aVF |

Initially, at step 350, the on-board surface EKG emulation system converts the most recently received internal voltage signals from the selected pairs of electrodes into a vector F. In the example of TABLE II, F is composed of ten values ($F_1$, $F_2$, . . . , $F_{10}$), each representing the latest digitized voltage from a respective one of the ten pairs of electrodes. At step 352, a set of weighting factors Km are retrieved from memory, for each combination of the internal leads "n" (where n=1, 2, . . . , 10) and for each surface lead to be emulated "m" (where m=1, 2, . . . , 12). Weighting factor $K_n^m$ generally represents the relative extent to which the internal voltage derived from electrode pair n influences the surface voltage at the surface lead m. Thus, for example, weighting factor $K_9^6$ represents the extent to which the internal voltage derived between the right atrial tip electrode and the right ventricular coil influences the surface voltage detectable at surface lead $V_6$.

By providing a separate weighting factor relating each of the ten electrode pairs with each of the twelve surface leads, the expected surface voltage for each of the twelve surface leads can be derived from the internal voltage signals. More specifically, the surface voltage for any give n location is obtained by summing each of the internal vo ltages times their respective weighting factors as follows:

$$E_1 = K_1^1 F_1 + K_2^1 F_2 + K_3^1 F_1 + \ldots + K_{10}^1 F_{10}$$

$$E_2 = K_1^2 F_1 + K_2^2 F_2 + K_3^2 F_1 + \ldots + K_{10}^2 F_{10}$$

$$E_{12} = K_1^{12} F_1 + K_2^{12} F_2 + K_3^{12} F_1 + \ldots + K_{10}^2 F_{10}$$

At step 354, the individual weighting factors are adjusted based upon posture, cardiac cycle, and/or respiratory cycle and, at step 356, the adjusted weighting factors are combined to yield a current representation of matrix $\underline{M}$. For example, if the patient is currently standing, particular weighting factors may be decreased in value wherea s others are increased to account for differences in the locations of the internal leads and the device ca n as a result of the differences in posture. The particular weighting factors to be adjusted and the specific amount of adjustment is determi ned in advance by the setup unit. Similar adjustments are made based upon the phase of the cardiac cycle and upon the phase of the respiratory cycle. The various adjustments to the weighting factors are determined in advance so the device need only apply predetermined adjustment amounts to the weighting factors to account for differences in the relative locations of the internal leads caused by differences in posture, cardiac cycle and respiratory cycle. Note, by taking into account posture, cardiac cycle, and respiratory cycle, $\underline{M}$ (and its individual weighting values) thereby becomes a function of all three (as well as time) and can be generally represented as $\underline{M}(p,c,r,t)$, where "p" represents posture, "c" represents phase of cardiac cycle and "r" represents phase of respiratory cycle.

Figure 7:
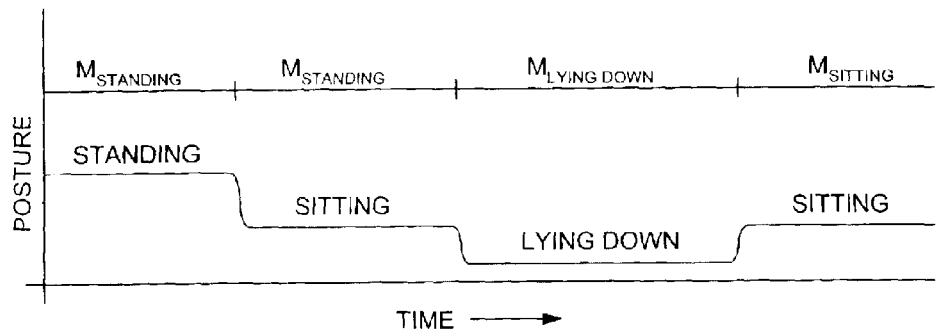
FIG. 7 is a diagram illustrating a typical sequence of postures and particularly illustrating the use of different conversion matrices for different postures in accordance with the technique of FIG. 6.

Alternatively, at step 355, rather than retrieving a single set of weighting factors then adjusting the weighting factors based upon posture, cardiac cycle, and respiratory cycle, the system can instead retrieve different set of weighting factor matrices depending upon the current posture, cardiac cycle, or respiratory cycle. FIG. 7 illustrates three separate postures, standing, sitting and lying down, and three separate matrices $\underline{M}_{STANDING}$, $\underline{M}_{SITTING}$ and $\underline{M}_{LYING\ DOWN}$ for use while the patient is found to be in the given posture. Although not shown, additional matrices may be provided for use during other postures, such as for use while walking or running. In addition, separate matrices may be used while the patient is lying down, depending upon whether the patient is prone or supine.

Figure 8:
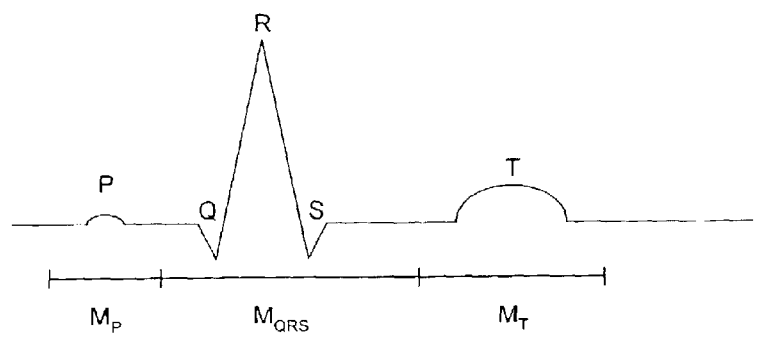
FIG. 8 is a diagram illustrating a typical cardiac cycle and particularly illustrating the use of different conversion matrices for different phases of the cardiac cycle in accordance with the technique of FIG. 6.

FIG. 8 illustrates three exemplary phases of the cardiac cycle, P-wave, QRS-complex, and T-wave and three separate matrices $\underline{M}_P$, $\underline{M}_{QRS}$ and $\underline{M}_T$ for use while the patient is found to be in the given cardiac cycle phase. Although not shown, additional matrices are provided for use during other phases of cardiac cycle, such as for use between the end of the T-wave and the beginning of the next P-wave. As noted, the use of different matrices for different portions of the cardiac cycle allows for compensation for changes in the relative positions of the electrodes caused by beating of the chambers of the heart. Additionally or alternatively, different matrices may be chosen for use during different phases of the cardiac cycle to emphasize particular signal vectors that are most useful during particular phases. For example, atrially involved signals such as $F_2$, $F_7$, $F_8$ and $F_9$ generally give a better presentation of the P-wave than other signals as the P-wave originates in the atrium. Conversely, signals that are primarily associated with the ventricles such as $F_5$ and $F_6$ generally make better sources for emulating the QRS complex, which is primarily derived in the ventricles, than other signals. Similarly, the T-wave is generally best derived from ventricular signals. Moreover, the first part of the R-wave, i.e., the Q-wave, which generally represents signals generated in the apex of the ventricle, is best generated by electrodes near that apex such as the RV tip and ring and thus favor a heavy weighting for $F_4$. Conversely, signals later in the QRS such as the S-wave are best constructed from signals later in the activation cycles that are higher up in the ventricle, such as the signals involved in the coronary sinus, e.g. $F_6$ and $F_7$.

Figure 9:
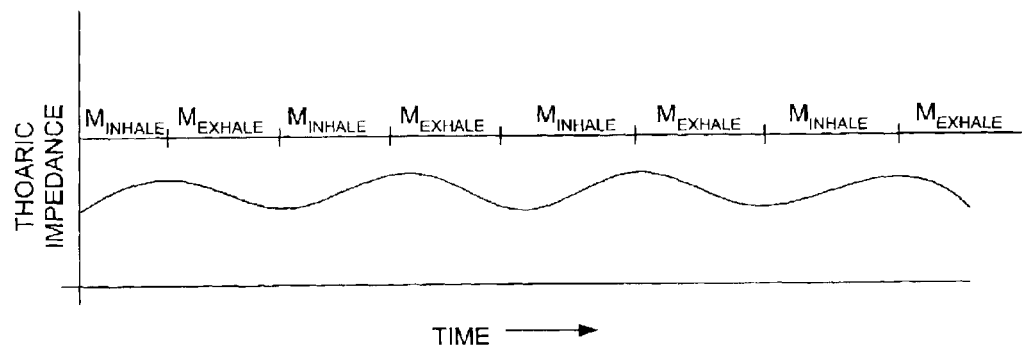
FIG. 9 is a diagram illustrating typical respiratory cycles and particularly illustrating the use of different conversion matrices for different phases of the respiratory cycles in accordance with the technique of FIG. 6.

FIG. 9 illustrates two exemplary phases of the respiratory cycle, inhalation and exhalation, and two separate matrices $\underline{M}_{INHALE}$, $\underline{M}_{EXHALE}$ for use while the patient is found to be in the given phase of the respiratory cycle. Again, additional matrices may be employed for further distinguishing among the different phases of the respiratory cycle. In addition, the depth of respiration can be detected and compensated. For example, different inhalation and exhalation matrices may be used depending upon whether the current breathing is shallow or deep.

Thus, a set of different matrices may be pre-stored in memory for use depending upon the current state of the patient, i.e. posture, cardiac cycle and respiratory cycle. If configured to only account for one of these factors, such as only posture, the on-board emulation system merely uses the single selected matrix. For example, if the on-board system is preprogrammed to only account for posture, and the patient is found to be standing, then the system simply retrieves and uses the $\underline{M}_{STANDING}$ matrix. If the on-board system is configured to account for a combination of these factors (i.e. to account for posture, cardiac cycle, and respiratory cycle), the system then, at step 356, combines the set of matrices applicable any given time to yield a single averaged matrix $\underline{M}$ for use in determining the output vector E. Also, a default matrix may be used in any situation wherein the implanted device cannot determine the posture, cardiac cycle phase, or respiratory phase or wherein the device identifies a posture, cardiac cycle phase, or respiratory phase for which no adjusted matrix is available (e.g. the device determines the patient to be currently running but no special running matrix $\underline{M}_{RUNNING}$ has been pre-stored.) As can be appreciated, a wide variety of techniques can be employed for generating a single matrix, which includes weighting factors taking into account posture, cardiac cycle, and respiratory cycle as well as perhaps other factors affecting the relative location of the internal leads. No attempt is made herein to describe all possible techniques.

In any case, at step 358, the on-board system calculates the latest value for E using the current $\underline{M}$ and the latest input voltage vector F via:

$$E = \underline{M} * F.$$

For the example where F includes ten values, the resulting matrix equation is as follows:

$$\begin{bmatrix} V_1 \\ V_2 \\ V_3 \\ V_4 \\ V_5 \\ V_6 \\ I \\ II \\ III \\ aVR \\ aVL \\ aVF \end{bmatrix} = \begin{bmatrix} K_1^1 & \cdots & K_{10}^1 \\ & \cdot & \\ & \cdot & \\ & \cdot & \\ \cdot & & \cdot \\ \cdot & & \cdot \\ \cdot & & \cdot \\ & & \\ & & \cdot \\ & \cdot & \\ & & \cdot \\ K_1^{12} & \cdots & K_{10}^{12} \end{bmatrix} \begin{bmatrix} F_1 \\ F_2 \\ F_3 \\ F_4 \\ F_5 \\ F_6 \\ F_7 \\ F_8 \\ F_9 \\ F_{10} \end{bmatrix}$$

Thus, following step 358, the on-board system has converted the latest internal voltage signals to expect surface voltages for each of the twelve leads of a standard 12-lead surface EKG thereby emulating a 12-lead surface EKG. Next, the onboard system seeks to verify that the emulation is reliable. At step 360, the onboard system periodically calculates cross-correlation values among the various elements of F detected during P-waves, R-waves and ST segments. More specifically, the set-up system calculates the cross-correlation between the elements of a given vector F detected during a P-wave, and then does the same for vectors detected during R-waves and ST-segments. Cross-correlations are not detected between P-wave vectors and R-wave vectors or between R-wave vectors and ST-segment vectors. These cross-correlation values are compared with baseline values previously determined during the set up phase and stored within the number of the implanted device. If there is an adequate match between the new cross-correlation values and the baseline values, then the emulated surface EKG is deemed reliable, step 364. If, however, the new cross-correlation values differ significantly from the baseline values (e.g.±25%), then the emulated surface EKG is deemed unreliable, step 366. If unreliable, an appropriate warning signal is transmitted along with the surface EKG signals to the external programmer (during step 318 of FIG. 5) to thereby advise the physician that the emulated surface EKG cannot be relied upon. Accordingly, the physician then employs a standard external surface EKG system to detect the surface EKG. Also, at that time, the physician is advised to recalibrate the weighting values and the baseline cross-correlation values by having the external programmer repeat the setup procedure, which will be explained below.

Note that any unreliability in the emulated surface EKG may be caused by lead dislodgment or may be indicative of cardiac conduction abnormality in the patient. Accordingly, the physician is also advised to X-ray the patient to verify proper lead location. If the leads are determined to be in their proper locations, then the physician is advised that the emulated surface EKG may have been rendered unreliable due to a cardiac conduction abnormality in the patient or other medical factors. In this manner, the surface EKG emulation procedure also serves as a method for detecting lead dislodgment or for detecting cardiac conduction abnormalities in the patient. Finally, if the implanted device is configured to control its internal functions based, in part, upon the emulated surface EKG and the emulated EKG is deemed unreliable, then the emulated EKG is not used to control device functions.

Programmer/Implanted Device Interface

Referring to FIGS. 10 and 11, two separate techniques for generating an emulated surface EKG under the control of an external programmer will now be described. In the example of FIG. 10, the conversion of internal voltage signals to emulated surface EKG signals is performed by the implanted device under the control of the external programmer and the emulated signals are transmitted to the external programmer for displaying further processing. In the example of FIG. 11, the conversion of internal signals into emulated EKG signals is performed by the external programmer using internal signals transmitted from the implanted device. In both figures, steps performed by the external programmer are shown on the left whereas steps performed by the implanted device are shown on the right.

Referring first to FIG. 10, at step 400, the external programmer, pursuant to commands entered by the physician or other trained medical personnel, transmits signals to the implanted device controlling the implanted device to begin emulation of the 12-lead surface EKG. At step 402, the implanted device receives the control signals and begins to emulate surface EKG signals using internal electrical cardiac signals in accordance with the technique described above in FIGS. 5–9. Conversion of internal electrical signals into surface EKG signals employs conversion matrices already stored within the implanted device by virtue of a previous setup operation. The implanted device also stores previously calculated baseline cross-correlation values for use in verifying the reliability of the emulated surface EKG. At step 404, the implanted device generates new cross-correlation values for comparison with the stored baseline values to verify reliability of the surface EKG. At step 406, the implanted device continuously transmits the 12-lead surface EKG signals to the external programmer along with a periodic indication of the reliability of the signals. Note that the implanted device transmits each of the twelve separate surface EKG signals, and not merely a single combined surface EKG signal.

The twelve emulated surface EKG signals are received by the external programmer, at step 408, along with the periodic indication of the reliability of the emulation. Assuming that the emulated surface EKG is reliable then, at step 410, the external device displays the surface EKG for review by the physician, who can additionally control the external programmer to printout the surface EKG, store the EKG, or manipulate the EKG as desired. In particular, since each of the twelve individual surface EKG signals are generated by the conversion process and are received by the external programmer, any conventional technique for processing and evaluating the 12-lead surface EKG signals may be utilized. In this regard, otherwise conventional techniques for filtering, enhancing, or analyzing the individual signals of the emulated 12-lead surface EKG may be exploited. Hence, the programmer is not limited to merely displaying a combined surface EKG.

If the surface EKG signals are deemed to be unreliable then, at step 412, the external programmer displays an appropriate warning signal to physician and, at step 414, displays recommendations to physician advising the physician to recalibrate the emulation system of the implanted device and to perform a chest X-ray to detect possible lead displacement. In either case, at step 416, again subject to control by the physician, the external programmer eventually controls implanted device to terminate emulation of the surface EKG. The termination control signals are received and processed by the implanted device at step 418, which deactivates the on-board surface EKG emulation system.

Referring to FIG. 11, the alternative technique wherein the external programmer performs the actual conversion of internal cardiac electrical signals into emulated surface EKG signals will now be briefly described. Many of the steps of FIG. 11 are similar or identical to those of FIG. 10 and only pertinent differences will be described in detail. At step 450, control signals are transmitted from the external programmer to the implanted device, which, at step 452, responds by generating internal electrical cardiac signal vectors. The signal vectors are transmitted continuously from the implanted device to the external programmer beginning at step 454. Also at step 454, if the emulation system is configured to take into account factors affecting lead location, the implanted device also transmits signals representative of those factors, i.e. the device transmits signals identifying current posture, cardiac cycle phase and respiratory phase. Alternatively, the implanted device transmits raw signals from which these factors can be derived, such as raw 3-D accelerometer signals and the like. The external programmer receives the internal signal vectors and other signals, at step 456, and, using the techniques described above in connection with FIGS. 5–9, converts the internal signals to emulated 12-lead surface EKG signals using previously generated conversion matrices. At step 458, the external programmer verifies the reliability of the emulated surface EKG signals by comparing cross-correlation values with baseline cross-correlation values. As in the previous example, if the surface EKG is deemed reliable, the surface EKG is displayed or otherwise manipulated at step 460. If the emulated surface EKG is deemed unreliable, appropriate warning signals are displayed at steps 462 and 464. Ultimately, subject to the control of the physician, surface EKG emulation is eventually terminated at steps 466 and 468.

Set-up Technique

Figure 12:
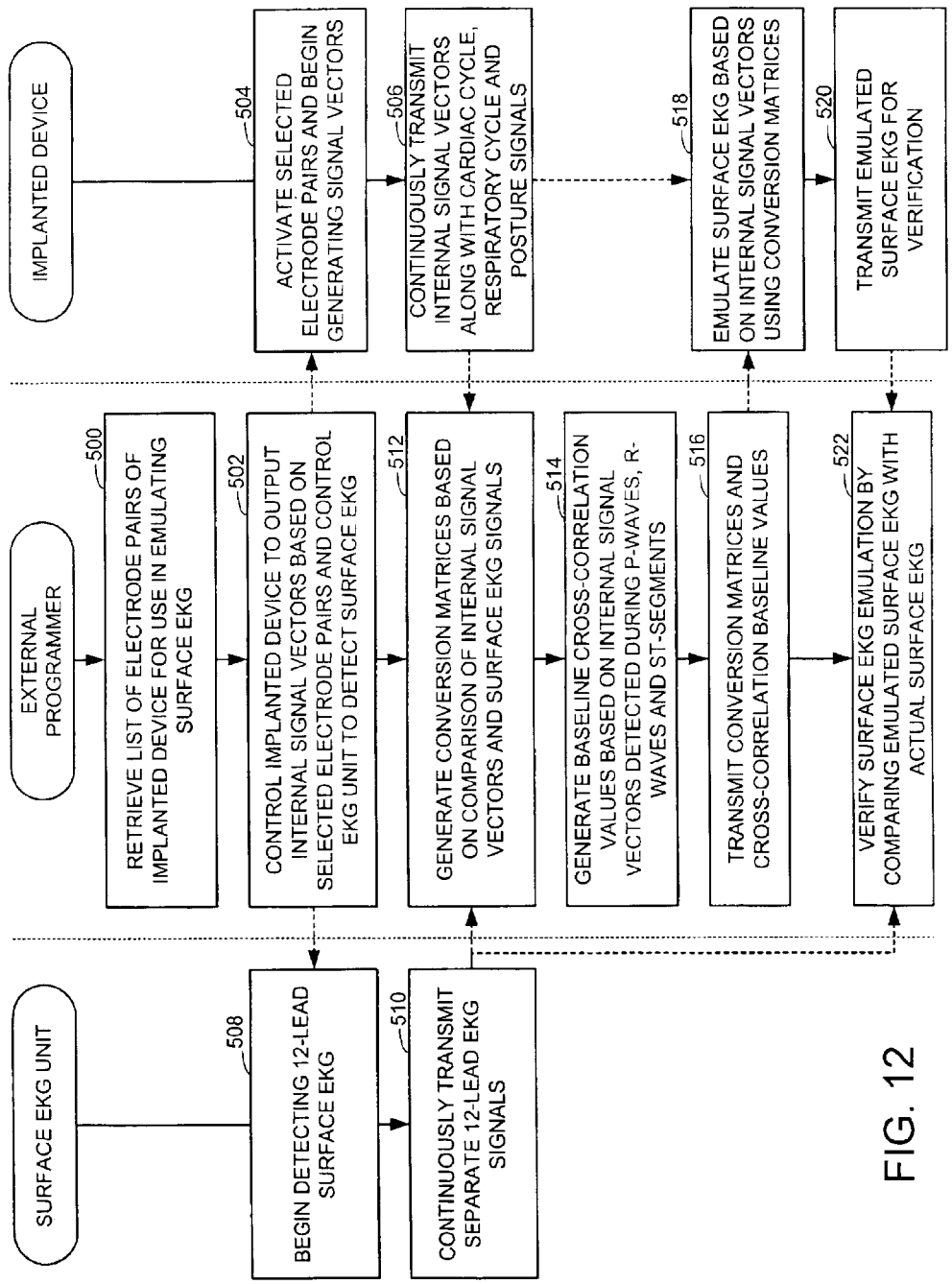
FIG. 12 is a flow chart providing an overview of an exemplary set-up technique performed by the external system of FIG. 4 for pre-calculating conversion matrices and cross-correlation values for subsequent use either by the external system itself or by the implanted device of FIG. 3.

Referring to FIG. 12, an exemplary setup and calibration technique for pre-calculating comparison matrices and baseline cross-correlation values for use with the techniques described above will now be described. Briefly, the set up technique employs actual (i.e. non-emulated) surface EKG signals received from an external surface EKG system for use in calibrating the conversion matrices. In the example of FIG. 12, it is assumed that the conversion matrices are ultimately transmitted to the implanted device for use therein. Alternatively, however, the conversion matrices may be retained within the external programmer for use in converting internal electrical cardiac signals received from the implanted device into emulated surface EKG signals within the external programmer.

Initially, at step 500, the external programmer retrieves a selected list of electrode pairs for use in generating emulated surface EKG signals. This list may be input by the physician or may be retrieved from memory. As noted, a wide variety of pairs of electrodes may be designated for use in performing the surface EKG emulation. In the example described above in connection with FIGS. 5–9, ten electrode pairs are utilized. At step 502, the external programmer controls the implanted device to begin generating and transmitting internal electrical cardiac signals and also controls an external surface EKG system to begin detecting and transmitting conventional 12-lead surface EKG signals. The implanted device, at step 504, activates the selected electrode pairs and begins to detect internal electrical cardiac signal vectors, which are transmitted to the external programmer beginning at step 506. In addition, at step 506, if the emulation system is to be calibrated to take into account factors affecting lead location, the implanted device also transmits signals representative of those factors, i.e. posture, cardiac cycle phase and respiratory phase. Alternatively, the implanted device transmits raw signals from which these factors can be derived, such as raw 3-D accelerometer signals and the like. In any case, simultaneously, the surface EKG unit, at step 508, begins detecting 12-lead surface EKG voltage signals, which are continuously transmitted to the external programmer beginning at step 510. Thus, the external programmer receives both the internal electrical cardiac signal vectors from the implanted device and actual 12-lead surface EKG voltage signals from the external surface EKG unit. At step 512, the external programmer generates conversion matrices based on a comparison of the internal cardiac signal vectors and the 12-lead surface EKG signals.

To generate a single conversion matrix $\underline{M}$ for use if factors affecting lead location are not to be taken into account, the set-up system represents the signal vectors received from the implanted device as a time-varying vector F(t) having individual elements corresponding to the selected pairs of electrodes. The set-up system converts the surface EKG signals received from the 12-lead EKG into a time-varying vector E(t) having individual elements corresponding to the twelve surface leads. The set-up system then generates and records a time-varying conversion matrix $\underline{M}(t)$ of weighting factors by calculating:

$$M(t) = E(t) * F^{-1}(t).$$

The set-up system then averages the $\underline{M}(t)$ over some period of time to yield a single fixed matrix $\underline{M}$. To ensure that $\underline{M}$ properly converges on stable values, the set-up system periodically solves for fixed matrix $\underline{M}$ by averaging $\underline{M}(t)$ using the data received thus far. The set-up system then compares the latest version of fixed matrix $\underline{M}$ with previous versions and evaluates the magnitude of difference therebetween. If the magnitude of the difference is below some predetermined threshold value, the matrix is deemed to have converged, and the calibration process is terminated. Otherwise, the set-up system continues to process data until the matrix converges to stable values. The threshold value for establishing conversion may be experimentally determined using routine techniques.

Preferably, however, to generate multiple conversion matrices for use, for example, if posture or other factors affecting lead location are to be taken into account, the following procedure is performed. As before, signal vectors received from the implanted device are represented as a time-varying vector F(t) and the set-up system converts the surface EKG signals received from the 12-lead EKG into a time-varying vector E(t). The set-up system also generates and records a time-varying conversion matrix $\underline{M}(t)$ of weighting factors by calculating: $M(t)=E(t)*F^{-1}(t)$. Additionally, though, the set-up system tracks the factors affecting lead location, such as the current posture, and labels various individual matrices out of the collection of time-varying matrices $\underline{M}(t)$ according to the current state of the factor affecting lead location. For example, if posture is to be taken into account, the set-up system labels matrix $\underline{M}(t_1)$ as a "standing" matrix if the patient was deemed to be standing at time $t_1$. The set-up system labels matrix $\underline{M}(t_2)$ as a "sitting" matrix if the patient was deemed to be sitting at time $t_2$, and so on and so forth. Note that many individual instances of matrix $\underline{M}(t)$ will not be labeled because the patient may be transitioning from one posture to another and hence the current posture will be indeterminate. However, all matrices $\underline{M}(t)$ generated while the posture of the patient could be determined are labeled using this technique.

Then, rather than averaging all matrices $\underline{M}(t)$, the set-up system averages only those matrices assigned the same posture label. Hence, all the matrices labeled as "standing" matrices are averaged together to yield a single $\underline{M}_{STANDING}$ matrix. All the matrices labeled as "sitting" matrices are averaged together to yield a single $\underline{M}_{SITTING}$ matrix. All matrices that were not labeled are averaged to field a default matrix $\underline{M}_{DEFAULT}$ to be used when posture cannot be determined. The set-up system continues to process data until each separate posture matrix converges to stable values. During this process, the patient is asked to assume various postures (standing, sitting, lying down) so that the setup system can input and process data for each particular posture to be taken into account.

Similar techniques are used to generate matrices for the other factors of respiration and cardiac cycle. If only one factor is to be taken into account (i.e. either posture only or respiration only or cardiac cycle only), then only one type of label is required and only one set of conversion matrices are generated, such as the aforementioned posture-based matrices. If multiple factors are to be taken into account at the same time (such as posture and respiration), then each conversion matrix is assigned multiple labels (such as standing/inhaling, standing/exhaling, sitting/inhaling, sitting/exhaling, etc.) In one exemplary technique, only matrices having the exact same pair of labels are averaged together. In other words, the set-up system generates an averaged $\underline{M}_{SITTING/INHALATION}$ matrix, an averaged $\underline{M}_{SITTING/EXHALATION}$ and so on. The setup system does not average together matrices that share only one label in common. Then, during actual EKG emulation, the emulation system retrieves the single conversion matrix appropriate for use at any give time based on both respiration and posture. Alternatively, all matrices having a common posture label are averaged together (even though they may not share the same respiration label) and all matrices having a common respiration label are averaged together (even though they may not share the same posture label). Then, during actual EKG emulation, the separate matrices are averaged together as needed. This reduces the total number of conversion matrices that will need to be stored for subsequent use. However, more data may need to be processed before the conversion matrices converge to a stable value or a lesser degree of convergence may need to be tolerated.

If, instead of using separate conversion matrices to account for factors affecting lead location, separate adjustment values are instead to be applied to the individual weighting factors of a single conversion matrix $\underline{M}$, generally similar techniques are employed to generate the adjustment values. For example, individual weighting factors may be labeled in a similar manner as described above, then adjustment factors are generated based on an examination of weighting factors that have like labels. As can be appreciated, a variety of techniques may be used for generating separate matrices or separate adjustment values to account for the various factors affecting lead location and no attempt is made herein to describe all such techniques.

In yet another alternative embodiment, the $\underline{M}$ matrices are calibrated using the timing of the cardiac events (P, Q, R, S, T) detected by the 12-lead surface EKG but not the amplitude values detected. For example, when the surface EKG indicates that an atrial contraction has occurred, the F signal vectors are weighted according to their relative strengths at that point, with the stronger signals being more representative of the P-wave. Proximity to the origin of the P-wave may also be factored into the weighting.

In any case, once the conversion matrix or matrices have been generated then, at step 514, the external programmer generates baseline cross-correlation values based on the internal electrical signals received from implanted device as detected during P-waves, R-waves and ST-segments. The cross-correlation values may be generated as follows. The P-waves, R-waves and SR-segments are identified in the surface EKG received from the external unit. The set-up system calculates cross-correlation values among the various elements of F(t) detected during the P-waves, R-waves and ST segments. For example, for a given F vector detected during a P-wave, cross-correlations are calculated between the elements of that vector. The cross-correlation is calculated using conventional mathematical techniques. Then, the cross-correlation values calculated for all vectors detected during a P-wave are averaged together to yield a single baseline P-wave cross-correlation value. The same is done for signals vectors detected during R-waves and ST-segments. As with the calculation of the matrix weighting factors, this technique is preferably performed until the cross-correlation baseline values converge on some stable value. In any case, the set-up system thereby generates three cross-correlation baseline values, one for P-waves, one for R-waves and one for ST-segments.

Figure 6:
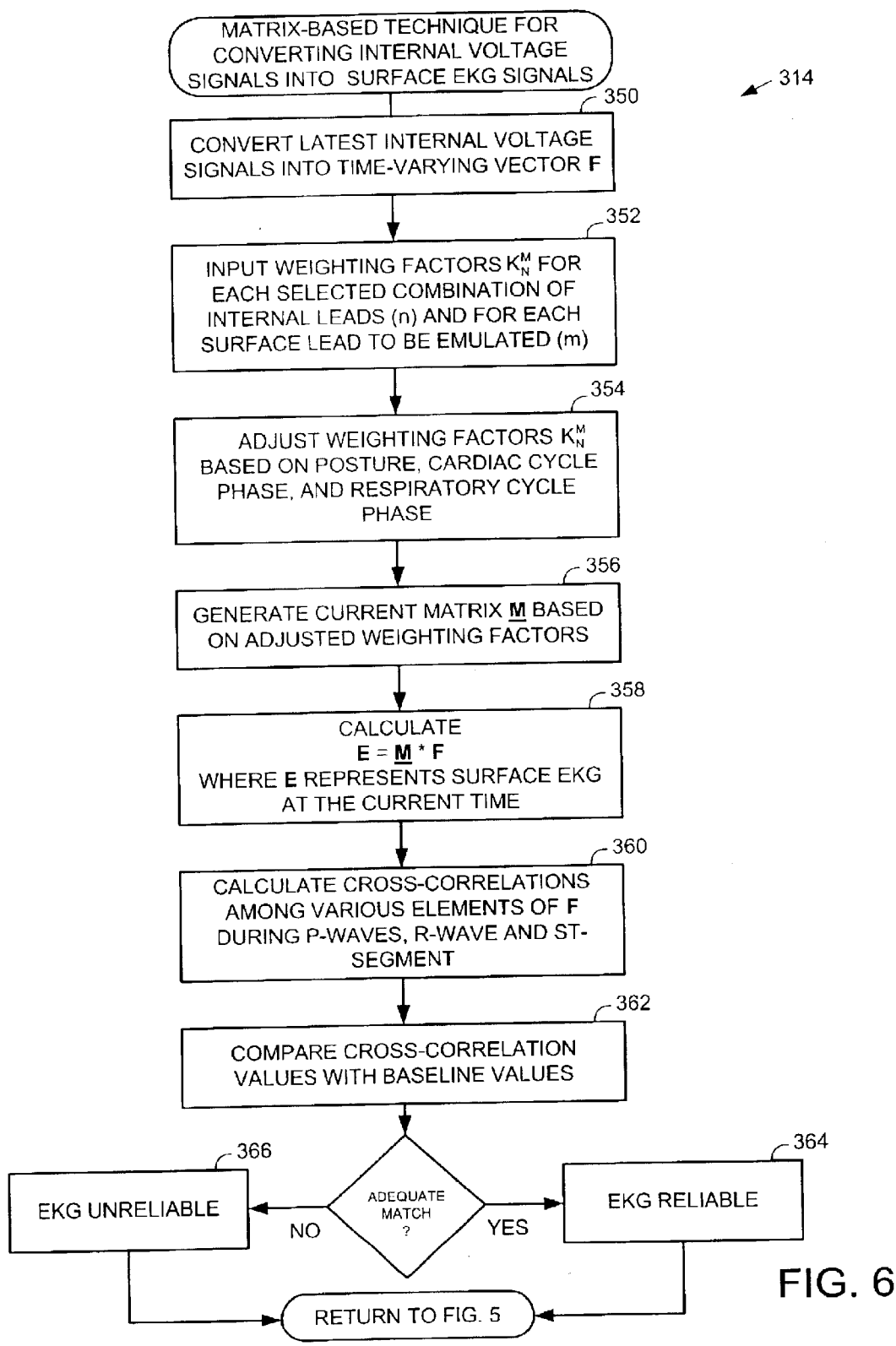
FIG. 6 is a flow chart providing details of the exemplary matrix-based emulation technique for use with FIG. 5.

As explained above in connection with steps 360 and 362 of FIG. 6, during EKG emulation, the baseline values are compared against newly calculated cross-correlation values to verify emulation reliability. Although described with respect to an exemplary technique exploiting cross-correlations among P-waves, R-waves and ST-segments, other features of the EKG can instead be used. In addition, if factors affecting lead location are to be taken into account, separate baseline correlation values can be calculated for the different states of those factors. In other words, one P-wave baseline cross-correlation value may be calculated for use while the patient is standing and a separate one while the patient is sitting. However, that is typically not necessary since the reliability verification technique using the cross-correlation values only seeks to detect significant changes in the cross-correlation values (particularly caused by lead dislodgment) and therefore the technique need not be extremely precise.

Then, step 516, the external programmer transmits the conversion matrices and cross-correlation baseline values to the implanted device for storage therein. The implanted device is programmed to immediately begin emulating surface EKG signals using the new conversion matrices and the emulated signals are transmitted back to the external programmer, at step 520, for comparison against simultaneously-received external surface EKG signals received directly from the surface EKG unit, at step 522. The external programmer compares the emulated surface EKG signals with the actual surface EKG signals to verify that the emulation of the surface EKG is sufficiently accurate. Although not specifically shown in FIG. 12, if the emulation is deemed to be inaccurate, then the setup process is repeated, perhaps using a different set of electrode pairs, until accurate emulation is achieved.

Thus, FIG. 12 provides an overview of a technique for calibrating the on-board emulation system of the implanted device to generate emulated surface EKG signals based on internal electrical cardiac signals. The general technique of FIG. 12 may also be applied in circumstances wherein the external programmer performs the actual conversion of internal electrical signals into surface EKG signals. In that alternative embodiment, the external programmer merely stores the conversion matrices and cross-correlation baseline values within internal memory for subsequent use. In either case, during subsequent follow-up sessions between the patient and physician, the physician need no longer utilize a surface EKG system and can instead use the emulated surface EKG (assuming that the cross-correlation values to verify continued reliability of the emulation process). Hence, the patient need no longer be burdened with having the ten surface EKG electrodes mounted to his or her chest. Time is saved for both the patient and the physician, overall medical costs are reduced, and possible embarrassment or discomfort to the patient is avoided. In addition, as noted, the emulation process allows for detection of possible internal lead dislodgment as well as possible adverse changes in electrical cardiac activity within the patient, which might not otherwise be detected when using a conventional external surface EKG system.

What have been described are various techniques for classifying cardiac electrical events and for adjusting or administering therapy based thereon. In general, the embodiments described herein are merely illustrative of the invention and should not be construed as limiting the scope of the invention, which is to be interpreted in accordance with the claims that follow.

What is claimed is:

1. A method performed by an external programmer in combination with an implantable cardiac stimulation device implanted within a patient and a multiple-lead surface electrocardiogram (EKG) unit, the method comprising:

inputting separate initial multiple-lead surface EKG signals from the EKG unit detected using separate surface electrodes attached to the patient;

inputting initial internal electrical cardiac signals sensed by the implanted device using internal electrodes;

generating, based on a comparison of the initial surface EKG signals and the initial internal cardiac signals, a set of conversion values for converting additional internal cardiac signals into separate multiple-lead surface EKG signals; and emulating separate multiple-lead surface EKG signals based on additional internal electrical cardiac signals using the conversion values such that the surface EKG unit is no longer needed.

2. The method of claim 1 wherein the surface EKG unit is a 12-lead surface EKG and wherein generating the set of conversion values is performed to generate a set of values for converting internal electrical cardiac signals into each of the twelve signals associated with the 12-lead surface EKG.

3. The method of claim 1 wherein generating the set of conversion values comprises converting the initial internal cardiac signals into a time-varying vector F(t) having individual elements corresponding to the pairs of electrodes;

converting the initial surface EKG signals into a time-varying vector E(t) having individual elements corresponding to the surface leads;

generating a time-varying conversion matrix $\underline{M}(t)$ of weighting factors by calculating $\underline{M}(t)=E(t)*F^{-1}(t)$; and averaging the time-varying conversion matrix $\underline{M}(t)$ over time to yield a single fixed matrix $\underline{M}$.

4. The method of claim 3 wherein the pairs of electrodes includes N pairs of electrodes and the surface EKG includes M surface leads; and wherein F(t) has N elements, n=1, 2, ..., N; E(t) has M elements, m=1, 2, ..., M; and matrix $\underline{M}(t)$ is an N by M matrix containing weighting factors $K_n^m$.

5. The method of claim 3 further comprising generating verification values for use in evaluating the reliability of the emulation of the multiple-lead surface EKG signals.

6. The method of claim 5 wherein generating verification values comprises
identifying like phases of a plurality of cardiac cycles of the patient based on the internal electrical cardiac signals;
generating cross-correlation values representative of cross-correlations between elements of vector F(t) during like phases of the plurality of cardiac cycles;
averaging the cross-correlation values to yield baseline cross-correlation values for use as verification values.

7. The method of claim 1 further comprising
inputting a signal representative of factors affecting the positions of the internal electrodes; and
wherein the step of generating a set of conversion values is performed to generate separate sets of conversion values based upon the factors affecting the positions of the electrodes.

8. The method of claim 7 wherein the factors affecting the positions of the electrodes include one or more of: phase of a respiratory cycle of the patient, phase of a cardiac cycle of the patient, and posture of the patient.

9. The method of claim 7
wherein the signal representative of the factors affecting the positions of the electrodes specifies the phase of the cardiac cycle of the patient; and
wherein the step of generating separate sets of conversion values generates separate sets distinguishing among, at least, P-waves, QRS-complexes and T-waves.

10. The method of claim 7
wherein the signal representative of the factors affecting the positions of the electrodes specifies the phase of the respiratory cycle of the patient; and
wherein the step of generating separate sets of conversion values generates separate sets distinguishing between, at least, inhalation and exhalation.

11. The method of claim 7
wherein the signal representative of the factors affecting the positions of the electrodes specifies the posture of the patient; and
wherein the step of generating separate sets of conversion values generates separate sets distinguishing among, at least, standing, sitting and lying down.

12. The method of claim 1 wherein the method further comprises transmitting the conversion values to the implanted device for use therein.

13. A method performed by an external programmer in combination with an implantable cardiac stimulation device implanted within a patient and a multiple-lead surface electrocardiogram (EKG) unit, the method comprising:
inputting separate initial multiple-lead surface EKG signals from the EKG unit detected using separate surface electrodes attached to the patient;
inputting initial internal electrical cardiac signals sensed by the implanted device using internal electrodes;
generating, based on a comparison of the initial surface EKG signals and the initial internal cardiac signals, a set of conversion values for converting additional internal cardiac signals into separate multiple-lead surface EKG signals;
transmitting the conversion values to the implanted device for use therein to emulate separate multiple-lead surface EKG signals based on additional internal electrical cardiac signals; and
receiving and displaying emulated separate multiple-lead surface EKG signals generated by the implanted device.

14. In an external programmer for use with an implantable cardiac stimulation device implanted within a patient and a multiple-lead surface electrocardiogram (EKG) unit, a system comprising:
a telemetry system operative to input separate initial multiple-lead surface EKG signals from the EKG unit detected using separate surface electrodes attached to the patient;
the telemetry system also operative to input initial internal electrical cardiac signals sensed by the implanted device using internal electrodes; and
a set-up system operative to generate, based on a comparison of the initial surface EKG signals and the initial internal cardiac signals, a set of conversion values for converting additional internal cardiac signals into separate multiple-lead surface EKG signals.

15. The system of claim 14 further comprising:
an on-board surface electrocardiogram (EKG) emulation system operative to emulate separate multiple-lead surface EKG signals using the conversion values applied to additional input cardiac signals.

16. In an external programmer for use with an implantable cardiac stimulation device implanted within a patient and a multiple-lead surface electrocardiogram (EKG) unit, a system comprising:
means for inputting separate initial multiple-lead surface EKG signals from the EKG unit detected using separate surface electrodes attached to the patient;
means for inputting initial internal electrical cardiac signals sensed by the implanted device using internal electrodes;
means for generating, based on a comparison of the initial surface EKG signals and the initial internal cardiac signals, a set of conversion values for converting additional internal cardiac signals into separate multiple-lead surface EKG signals; and
means for emulating separate multiple-lead surface EKG signals based on additional internal electrical cardiac signals using the conversion values.

* * * * *